United States Patent
Yakovenko et al.

(10) Patent No.: US 12,387,817 B2
(45) Date of Patent: Aug. 12, 2025

(54) SEQUENCE VARIATION DETECTION USING DEEP LEARNING

(71) Applicant: NVIDIA Corporation, Santa Clara, CA (US)

(72) Inventors: Nikolai Yakovenko, Palo Alto, CA (US); Johnny Israeli, San Jose, CA (US); Avantika Lal, Burlingame, CA (US); Michael Vella, Princes Risborough (GB); Zhen Hu, Redwood City, CA (US)

(73) Assignee: NVIDIA Corporation, Santa Clara, CA (US)

( * ) Notice: Subject to any disclaimer, the term of this patent is extended or adjusted under 35 U.S.C. 154(b) by 980 days.

(21) Appl. No.: 16/410,978

(22) Filed: May 13, 2019

(65) Prior Publication Data

US 2020/0365234 A1 Nov. 19, 2020

(51) Int. Cl.
| | |
|---|---|
| *G16B 30/00* | (2019.01) |
| *G06N 3/08* | (2023.01) |
| *G06N 20/00* | (2019.01) |
| *G16B 5/00* | (2019.01) |
| *G16B 20/20* | (2019.01) |
| *G16B 40/00* | (2019.01) |
| *G16B 40/20* | (2019.01) |

(52) U.S. Cl.
CPC ............. *G16B 30/00* (2019.02); *G06N 3/08* (2013.01); *G06N 20/00* (2019.01); *G16B 5/00* (2019.02); *G16B 20/20* (2019.02); *G16B 40/00* (2019.02); *G16B 40/20* (2019.02)

(58) Field of Classification Search
CPC .......... G16B 5/00; G16B 20/20; G16B 30/00; G16B 40/00; G16B 40/20; G06N 3/08; G06N 20/00
See application file for complete search history.

(56) References Cited

U.S. PATENT DOCUMENTS

| | | |
|---|---|---|
| 9,922,285 B1 | 3/2018 | Glode et al. |
| 2016/0283654 A1 | 9/2016 | Ye et al. |
| 2016/0283655 A1 | 9/2016 | Ye et al. |
| 2017/0249547 A1 | 8/2017 | Shrikumar et al. |
| 2019/0114544 A1* | 4/2019 | Sundaram ............... G16B 20/00 |
| 2019/0114547 A1* | 4/2019 | Jaganathan .......... G06N 3/0481 |
| 2019/0220704 A1* | 7/2019 | Schulz-Trieglaff .... G16B 20/20 |

FOREIGN PATENT DOCUMENTS

| | | |
|---|---|---|
| WO | 2016201564 A1 | 12/2016 |
| WO | 2018006152 A1 | 1/2018 |
| WO | 2018094360 A2 | 5/2018 |
| WO | WO-2019200338 A1 * | 10/2019 ........... G06K 9/6267 |

OTHER PUBLICATIONS

Szegedy, C., Vanhoucke, V., Ioffe, S., Shlens, J. and Wojna, Z., 2016. Rethinking the inception architecture for computer vision. In Proceedings of the IEEE conference on computer vision and pattern recognition (pp. 2818-2826). (Year: 2016).*
European Search Report for EP application No. 20167225.0, Aug. 20, 2020, p. 1-9.
Ruibang Luo et al., "A multi-task convolutional deep neural network for variant calling in single molecule sequencing," Nature Communications, vol. 10, No. 1, Mar. 1, 2019; abstract, p. 8 right-hand column.
Ryan Poplin et al., "A universal SNP and small-indel variant caller using deep neural networks," Nature Biotechnology, Sep. 24, 2018; abstract; figure 1.
Nielsen et al., "Genotype and SNP calling from next-generation sequencing data," Nat. Rev. Genet. Jun. 2011; 12(6): 443-451.
Freed et al., "The Sentieon Genomics Tools—A fast and accurate solution to variant calling from next-generation sequence data," biorxiv preprint first posted online Mar. 10, 2017; doi: http://dx.doi.org/10.1101/115717, p. 1-11.
Goodwin et al., "Coming of age: ten years of next-generation sequencing technologies," Nature Reviews Genetics, vol. 17: 333-351 (Jun. 2016).
Hiranuma et al., "DeepATAC: A deep-learning method to predict regulatory factor binding activity from ATAC-seq signals," bioRxiv preprint first posted online Aug. 6, 2017; doi: http://dx.doi.org/10.1101/172767, p. 1-5.
Israeli, "Deep Learning for Shallow Sequencing," presented at GTC Silicon Valley, Session S8602, Mar. 2018, p. 1-34.
Kelley et al., "Basset: learning the regulatory code of the accessible genome with deep convolutional neural networks," Genome Res. 2015 26:990-999.
Koh et al., "Denoising genome-wide histone ChIP-seq with convolutional neural networks," Bioinformatics, 33, 2017, i225-i233; doi: 10.1093/bioinformatics/btx243.
Poplin et al., "Creating a universal SNP and small indel variant caller with deep neural networks," bioRxiv preprint first posted online Dec. 14, 2016; doi: http://dx.doi.org/10.1101/092890, p. 1-24.

(Continued)

*Primary Examiner* — Olivia M. Wise
*Assistant Examiner* — Janna Nicole Schultzhaus
(74) *Attorney, Agent, or Firm* — FisherBroyles, LLP; Adam K. Whiting

(57) ABSTRACT

Methods, systems, and computer program products are disclosed that use embeddings of candidate variation information and deep learning models to accurately and efficiently detect variations in biopolymer sequencing data, particularly suboptimal sequencing data.

14 Claims, 5 Drawing Sheets

(56) References Cited

OTHER PUBLICATIONS

Schep et al., "chromVARar: inferring transcription-factor-associated accessibility from single-cell epigenomic data," Nature Methods, published online 21 2017; doi:10.1038/nmeth.4401, p. 1-9.

Thibodeau et al., "A neural network based model effectively predicts enhancers from clinical ATAC-seq samples," www.nature.com/ScientificReports (2018) 8:16048 | DOI:10.1038/s41598-018-34420-9; published online: Oct. 30, 2018, p. 1-15.

Vaswani et al., "Attention Is All You Need," arXiv:1706.03762v5 [cs.CL] Dec. 6, 2017; 31st Conference on Neural Information Processing Systems (NIPS 2017), Long Beach, CA, USA, p. 1-15.

Zhou et al., "Predicting effects of noncoding variants with deep learning-based sequence model," Nature Methods, 12 (10): 931-934; published online Aug. 24, 2015; doi:10.1038/nmeth.3547, p. 1-8.

Li et al., "The Sequence Alignment/Map format and SAMtools," Bioinformatics 25(16): 2078-2079 (2009).

The SAM/BAM Format Specification Working Group, "Sequence Alignment/Map Format Specification," version c0358f5, dated Jan. 30, 2019, available online at https://github.com/samtools/hts-specs, p. 1-21.

"The Variant Call Format (VCF) Version 4.2 Specification," version f305206, dated Sep. 22, 2018, available online at https://github.com/samtools/hts-specs, p. 1-28.

\* cited by examiner

400

SEQUENCE VARIATION DETECTION USING DEEP LEARNING

FIELD

The present disclosure relates generally to methods and systems for using embeddings and deep learning to detect variations in biopolymer sequencing data.

BACKGROUND

The human genome is the complete set of nucleic acid sequences for humans, encoded as DNA within the 23 chromosome pairs in cell nuclei and in a small DNA molecule found within individual mitochondria. The human genome consists of 6 billion base pairs that include both protein-coding DNA genes and noncoding DNA. The Human Genome Project published the first complete sequence of an individual human genome in 2001. Currently, thousands of human genomes have been completely sequenced, and many more have been mapped at lower levels of resolution. The resulting data are used worldwide in biomedical science, anthropology, forensics, and other branches of science. There is a widely held expectation that genomic studies will lead to advances in the diagnosis and treatment of diseases, and to new insights in many fields of biology, including human evolution.

Understanding the genetic basis of disease, however, requires that genomic DNA sequences of individuals are accurately and rapidly determined down to the single base pair level. This level of resolution in DNA sequencing allows the identification of natural variation in sequences that occurs between different individuals. These individual sites of sequence variation, commonly referred to as a single nucleotide variation (SNV) or single nucleotide polymorphism (SNP), exist throughout individual genomes and provide information potentially critical to the use of genomic sequence information across the full range of applications. SNP refers to a variation in a position of a genome sequence that occurs in different human population. For example, at a specific human genomic position the nucleotide C may appear in most humans, but in a minority of individuals an A may occur at the same genomic position. These two different nucleotides are referred to as alleles for the particular position of the genome. It is estimated that a SNP occurs on average every 300 bp across the human genome resulting in the average human genomic sequence having approximately 10 million SNPs relative to a reference genome.

SNPs generally refer to variants found in the genome of human germline cells. SNV is a more general term and can include the variation of a single nucleotide at a specific site that may occur in a somatic cell genome. Cancer cells represent a highly studied class of somatic cells that include SNVs that are believed to be critical to their pathological phenotype and diagnosis.

DNA sequencing technology has advanced greatly since the first determination of an individual human genome in 2000 which was estimated to have cost $2.7 billion. Currently, the most advanced high-throughput techniques are commonly referred to as "next generation sequencing" (NGS). NGS technologies have enabled large scale sequencing of the genomes of plants and animals and made the process of determining a whole genome sequence achievable in as little as a week for a cost of ~$1000.

NGS technologies generally work by simultaneously carrying out millions of individual overlapping sequencing reaction that each generate a short sequence or "read" of a few hundred base pairs in length. Determining the sequence requires multiple sequence reads covering each base position, and typically, it is desirable to have 30-fold redundancy of reads at each base position (i.e., "30X coverage"). Accordingly, NGS generates a large dataset composed of vast numbers of sequence reads. The sequence reads provided by NGS technologies, however, have relatively high error rates of ~0.1-10%. Processing of NGS thus requires highly involved statistical error analysis for each sample. The complexity of post-reaction processing of NGS sequence reads to account for and minimize errors creates great difficulties for the process of correctly identifying or "calling" the mutations or variants in a genome sequence.

The desire to distinguish true variations from errors present in NGS datasets has led to the development of methods and software tools for this purpose. Two widely used software tools for used calling variations, such as SNPs, SNVs, insertions, and deletions, from NGS datasets are the Genome Analysis ToolKit or "GATK" (available at: software.broadinstitute.org/gatk/) and SAMtools (Li et al., "The Sequence Alignment/Map format and SAMtools," Bioinformatics 25(16): 2078-2079 (2009)). These widely-used variant calling software tools use "classical" methods for aligning sequence reads, and bioinformatic analysis and machine-learning modeling of the aligned reads to call the variants. The "classical" bioinformatic and machine learning components of these software tools require labor-intensive "hand-crafting" of data features, which greatly limits their ability to generalize across sequencing datasets obtained from different types of sequencing machines and/or data having different depths of coverage. Moreover, the variant calling accuracy of the classical tools, such as GATK, deteriorates significantly when applied to sequencing datasets that are suboptimal (e.g., low coverage).

DeepVariant is a deep learning-based software tool developed to improve upon the classical variant calling tools (see e.g., Poplin et al., "Creating a universal SNP and small indel variant caller with deep neural networks," bioRxiv 092890; doi: doi.org/10.1101/092890; published Dec. 14, 2016). DeepVariant uses a convolutional neural network (CNN) to call genetic variation in aligned NGS read data by learning statistical relationships between images of read pileups around putative variants sites and ground-truth genotype calls. DeepVariant has been shown to outperform GATK on benchmark whole genomes with 30× sequencing depth and to generalize better to data from sequencing machines that had not been used during training. The accuracy of Deep-Variant for calling variants using low coverage sequencing data is unclear Thus, there remains a need for improved methods that decrease the cost, processing time, and sample requirements for high accuracy detection and classification of variations found in sequencing data.

DETAILED DESCRIPTION

Figure 1:
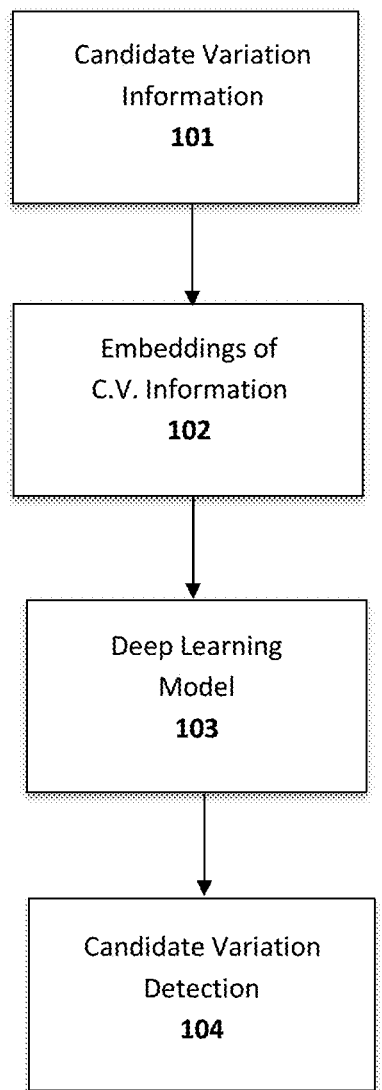
FIG. 1 depicts an overview flow diagram of exemplary operations for detecting candidate variations in embeddings of sequencing data in accordance with embodiments of the present disclosure.

Unless defined otherwise, all technical and scientific terms used herein have the same meaning as commonly understood by one of ordinary skill in the art to which the present invention pertains. Generally, the terms used to describe the techniques and procedures described herein are well understood and commonly employed by those of ordinary skill in the art, such as the common techniques and methodologies used for high-throughput (or next-generation) sequencing and for calling mutations (e.g., SNPs or SNVs) from this type of sequencing data. Such common techniques and methodologies for sequence data acquisition and mutation analysis are described in e.g., Goodwin et al., "Coming of age: ten years of next generation sequencing technology," Nat Rev Genet. 2016 June; 17(6):333-51; and Nielsen et al., "Genotype and SNP calling from next-generation sequencing data," Nat. Rev. Genet. 2011 June; 12(6): 443-451.

For purposes of interpreting this disclosure, where appropriate, a term used in the singular form will also include the plural form and vice versa. For the descriptions provided herein and in the appended claims, the singular forms "a", and "an" include plural referents unless the context clearly indicates otherwise. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of." Where a range of values is described, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Thus, where the stated range includes one or both of these limits, ranges excluding either or both of those included limits are also included in the invention. For example, "1 to 50," includes "2 to 25," "5 to 20," "25 to 50," "1 to 10," etc.

The ordinary artisan should appreciate that the methods, systems, and computer-readable medium products described herein provide many advantageous technical effects including improving the accuracy, speed, compactness, and overall efficiency of detecting variations in sequencing data, even suboptimal, low-coverage data, using a deep learning model. It should also be appreciated that the following specification is not intended as an extensive overview, and as such, concepts may be simplified in the interests of clarity and brevity.

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Use of Embeddings and Deep Learning to Classify Candidate Variations

The present disclosure provides methods, systems, and computer program products that use embeddings representing biopolymer sequence information (e.g., sequence reads) to detect candidate variations in these sequences.

Robust neural networks are known to result from training using dense vectors where all of values contribute to defining the "object" of interest. Many objects of interest, however, do not have a natural representation as a dense vector. For example, the plurality of biopolymer sequence reads resulting from high-throughput sequencing experiments are simply long strings of four letters representing the monomeric units of the biopolymer (e.g., nucleic acid bases, A, C, G, and T). An embedding is a mapping of a discrete object to a vector of real numbers. The dimensions and values of the embedding vectors are learned but do not otherwise have inherent meaning. Typically, initial real number values of an embedding are randomly generated and then the final embedding values are learned by neural network training. It has been found that the overall location, patterns, and distance between vectors in some learned embeddings can provide useful information. For example, similarity in vector space (e.g., the Euclidean distance or the angle between vectors) for learned embeddings of large sets of words has been found to be a robust and flexible measure of word similarity. Techniques and methods for generating and using embeddings of words and other discrete objects in deep learning models are well known in the art (see e.g., www-.tensorflow.org/guide/embeddings).

The use of learned embeddings of biopolymer sequence information has not previously been used to detect candidate variations in the sequences, such as mutations or simply experimental errors in the data. It is a surprising result of the present disclosure that a plurality of embeddings representing a plurality biopolymer sequence reads, can be used to determine an accurate classification of one or more candidate variations in the sequence. The methods, systems, and programs provide for increased efficiency, accuracy, and speed in classifying the candidate variations (e.g., calling SNPs) detected in the plurality of sequence reads typically generated in high-throughput sequencing of biopolymers by a range of sequencing machines. Moreover, the methods and systems of the present disclosure that use embeddings of sequence reads to detect variations in the sequence, can be processed using deep learning models to obtain accurate classification of the candidate variations even from suboptimal data (e.g., low coverage NGS data). Among the effects of the methods and systems disclosed herein are significant reductions in time and cost of obtaining biopolymer sequences, such as germline and somatic genomes, and greater accuracy in detecting the presence and identity of variations in those biopolymer sequences.

As described elsewhere herein, high-throughput biopolymer sequencing technologies provide extremely large, highly redundant, datasets comprising thousands or millions of sequence reads that have high rates of errors. The increasing use of these high-throughput sequencing technologies has given rise to a range of data analysis problems due to their large datasets and error rates. Among the challenging problems in dealing with any high throughput dataset of biopolymer sequence reads is the problem of detecting true variations in the sequence. These variations are of great scientific value but are hidden among false variations in the sequencing data. The errors can appear very similar to the true variations are difficult to characterize statistically, particularly across multiple experiments and instruments. The methods and systems of the present disclosure are directed to solving the problem of detecting whether a putative variation in a sequence read, or candidate variation, is a true difference in the sequence or just an error. The methods and systems of the present disclosure utilizing embeddings and deep learning can be applied to detecting candidate variations from any type of biopolymer sequencing data. Currently, high-throughput sequencing technologies for nucleic acid sequencing are in wide use. It is contemplated, however, that the methods and systems of the present disclosure can be applied to large datasets of sequence reads from any biopolymer, such as protein or carbohydrate sequence reads.

In some embodiments, the candidate variations detected using the methods and systems of the present disclosure can include sequence variants or mutations, such as SNPs, SNVs, and/or indels, that are identified in the large datasets of overlapping sequence reads corresponding to the multiple different nucleic acid molecules synthesized from separate portions of a template being sequenced. The problem of classifying candidate variations is encountered frequently in the massive datasets of overlapping sequence reads that are obtained from NGS experiments. A range of NGS technologies are known in the art. For a review of NGS technologies see e.g., Goodwin et al., "Coming of age: ten years of next generation sequencing technology," Nat Rev Genet. 2016 June; 17(6):333-51. It is contemplated that the methods and systems of the present disclosure can be used to classify variations from sequencing data obtained from any of the NGS technologies known in the art.

In some embodiments, the candidate variations detected using the methods and systems of the present disclosure can include variations between sequences corresponding to copies of the same molecule. Such variations occur due to errors during sequencing of the same molecule multiple times, for example, as in circular consensus sequencing (or "CCS"). See e.g., Wenger et al., "Highly-accurate long-read sequencing improves variant detection and assembly of a human genome," bioRxiv; posted Jan. 23, 2019 (doi: doi.org/10.1101/519025). Briefly, CCS is an NGS technology that uses a large, single circular nucleic acid construct that is repeatedly sequenced resulting in multiple sequence reads of the same molecule. These CCS sequence reads are typically much longer (e.g., average length ~10,000 to 100,000 bp). This greater length provides advantages for certain types of genome sequence analysis, but there relatively high rates of errors associated with these long sequence reads from CCS. The error-caused variations between the multiple sequence reads corresponding to the same sequence result in a problem in generating the true consensus sequence. Even though more measurements should in principle provide higher accuracy of consensus sequence, increasing the number of CCS sequence reads per target sequence results in decreased overall throughput of the CCS instrument. The present methods and systems using embeddings and deep learning can provide a higher accuracy consensus sequence generation from CCS datasets of fewer sequence reads. Generally, the problem of detecting candidate variations and generating an accurate consensus sequence from a dataset comprising multiple CCS sequence reads of the same large target nucleic acid molecule can be solved using the same methods and systems using embeddings and deep learning described for classifying candidate variations.

NGS technologies work by carrying out millions of sequencing reactions in parallel, and each reaction results in millions of "sequence reads," (also referred to herein as "reads" or "read sequences") that are typically a few hundred base pairs (bp) in length, although some NGS technologies, such as circular consensus sequencing (or "CCS") are able to produce long reads averaging 10,000 bp in length. The sequence reads correspond to short portions of the much larger sequence, such as an exome or a genome, that can be millions or billions of bp in length. The plurality of read sequences generated in an NGS dataset may not are not all contiguous portions of the much larger target sequence but rather are overlapping portions that cover the whole length of the target sequence. The overlapping nature of the sequence reads results in helpful data redundancy in an NGS experiment, but the level of redundancy at different portions of the sequence are not consistent. Currently, the standard accepted as the desired level redundancy for an accurate sequence is "30× coverage," which means that on average 30 separate sequence reads covering each base position of the sampled genome. Unfortunately, the massive number of parallel sequence reads have relatively high error rates on the order of 0.1% to 10%. Accordingly, further post-processing analysis of the errors is required to provide an accurate overall sequence for each sample. Moreover, 30× coverage is an average across the sequencing dataset. There are many locations in the dataset having far fewer (e.g., only 10) reads, and others having far more (e.g., 1000) reads. The high rate of errors in the numerous sequence reads together with the uneven level of coverage creates a particularly challenging problem when trying to use NGS sequencing data to accurately detect and confirm the presence of a true mutation or variant in a nucleic acid sequence, such as a single nucleotide variant (SNV), a single nucleotide polymorphism (SNP), or an indel.

In high-throughput sequencing datasets, differences or variations commonly occur between sequence reads and/or between a sequence read and a reference sequence. For example, millions of candidate variations are observed in a typical high-throughput sequencing dataset that spans a genome ("genome" refers to a full genome, or a portion of a genome, such as an exome). These observed variations in sequence reads may be due to an actual variant sequence (e.g., a mutation) or to some sort of experimental error (e.g., random error due to high noise). An observed, but unconfirmed, variation in a sequence read relative to other sequence reads, and/or relative to a reference sequence, is referred to as a "candidate variation." "Candidate variation detection" or "candidate variation classification," constitutes determining whether an observed candidate variation is a true variation in the sequence (e.g., a variant or mutation), or an error in the sequence (e.g., experimental noise). In the case of a candidate variation detection of a true variation in a sequence, the detection or classification can further comprise determining the type of variation (e.g., a substitution, an insertion, or a deletion in the sequence). Optionally, in the case of nucleic acid sequencing, detecting a candidate variation can further include determining whether the variation in the sequence occurs at one, two, or more alleles in a genome or exome. Accordingly, detection or classification of a candidate variation, in some embodiments, includes more than just a yes or no answer. For example, where there are two alleles (e.g., allele A and allele B) corresponding to gene sequence from a genome NGS dataset, detection of candidate variations can result in four possible answers corresponding to the possibility of a true sequence variant existing on either or both of the two distinct alleles—e.g., $Yes_A/Yes_B$, $No_A/Yes_B$, $Yes_A/No_B$, or $No_A/No_B$.

The problem of classifying numerous candidate variations is amplified when the source sequencing dataset being used to identify the candidate variations is suboptimal. "Suboptimal" refers to having a quality less than optimal, and "suboptimal candidate variations" refers to those candidate variations obtained from a sequencing dataset of less than optimal quality. Such a dataset typically includes suboptimal sequence read and thus susceptible to higher rates of observed variations that are either not detected, incorrectly detected, and/or otherwise mis-classified. Suboptimal candidate variation information can result from many sources detrimental to the quality of sequencing data, including the use of fewer sequence reads (e.g., low-coverage datasets), a limited amount of sample, and/or any source capable of introducing noise or error. The ability to use suboptimal candidate variation information he includes suboptimal sequence reads, however, can be desirable because suboptimal datasets can be obtained rapidly, thereby allowing for faster, cheaper sequencing experiments. Thus, the use of suboptimal dataset can provide for time and cost reductions that allow for more complete genomes of human individuals to be accurately determined. Accordingly, there is much to be gained in improving methods and systems for candidate variation classification.

The present disclosure provides methods and systems that use deep learning models to detect candidate variations from high-throughput sequencing data. In particular, the methods and systems can be used to generate embeddings of candidate variation information obtained from high-throughput sequencing datasets, including suboptimal sequencing datasets, such as low-coverage data obtained with less than 30× sequencing depth. By allowing accurate candidate variation detection with low-coverage data, the deep learning-based methods and systems of the present disclosure can facilitate faster, more efficient, and more cost-effective nucleic acid sequencing resources. Faster, more efficient sequencing can thus enable wider use of nucleic acid sequencing for medical applications such as personalized medicine and diagnostics.

The deep learning models and associated techniques used in the methods of the present disclosure are based on the use of neural networks, such as convolutional neural networks (CNNs), in computer-based systems. Such deep learning models have been used successfully to extract features and classify data in a wide range of applications, most notably, image, language, and speech recognition. In order to effectively process candidate variations derived from high-throughput sequencing datasets using a deep learning model, embeddings of the appropriate sequencing data are generated that facilitate the use of neural networks.

In some embodiments, the present disclosure provides a method comprising: generating a plurality of embeddings including a plurality of biopolymer sequence reads; and detecting one or more candidate variations in the sequence reads based at least in part on the plurality of embeddings.

FIG. 1 illustrates an overview flow diagram of the exemplary operations for generating a plurality of embeddings including sequence reads (particularly reads from suboptimal sequencing data) and detecting candidate variations in the sequence reads based in part on the embeddings, using methods and systems described present disclosure. Candidate variation information 101 (also referred to herein as "C.V. Information"), which includes a plurality of biopolymer sequence reads, is generated from standard sequencing data using any of the software tools well-known in the art for processing of sequencing data and making variant calls. Two of the most widely-used software tools for nucleic acid sequence datasets are GATK (i.e., the "genome analysis toolkit") which is available from the Broad Institute (software.broadinstitute.org/gatk/) and SAMtools (Li et al., "The Sequence Alignment/Map format and SAMtools," Bioinformatics 25(16): 2078-2079 (2009)). These software tools carry out "classical" variant calling by aligning the numerous sequence reads from a target sample to a reference genome, and then use bioinformatic analysis and machine-learning modeling of the aligned reads to generate candidate variations.

Candidate variation information, which includes a plurality of biopolymer sequence reads, and is useful in the methods and systems of the present disclosure can be generated from standard sequencing data using standard well-known software for calling variations. For example, a dataset of high-throughput NGS read sequences can be analyzed using and a corresponding reference sequence and classical variant calling software tools, such as GATK and SAMtools, to generate candidate variations. In some embodiments, the sequencing data used in the method is a low-coverage dataset having less than an optimal number of read sequences at each candidate variation location. Such suboptimal, low-coverage datasets are useful in the candidate variation classification methods of the present disclosure, and, in some embodiments, can include datasets having less than 30× coverage, less than 20× coverage, less than 15× coverage, or even lower coverage of a target genome sequence.

In some embodiments, the candidate variation information 101 used in the methods and systems of the present disclosure comprises a subset of the standard information found in the file formats generated by classical variant calling software tools, such as GATK and SAMtools, such as VCF and/or BAM files. For example, candidate variation information can be extracted from a variant call format (VCF) file. The VCF file that includes information about the specific candidate variation position and base call, the absolute location in the genome (e.g., detailing chromosomal site), and the quality of the base call in the read sequence (BQ). The VCF file also includes a compressed sequence alignment/map format (BAM) file that contains information about the read mappings/alignments and their quality, also referred to herein as read mapping quality (MQ). The VCF and BAM file formats are well known in the art and a complete description of each is publicly available online at e.g., github.com/samtools/hts-specs.

As noted above, not all of the candidate variation information generated by the standard variation calling software tools needs to be used in the deep-learning methods of the present disclosure. Indeed, it is an advantage of the presently disclosed methods that only selected data representing the candidate variation information 101 need to be used to generate the embeddings of candidate variation information 102, including embeddings of the plurality of sequence reads, that can then be processed by the deep learning model 103 to generate the output of detecting (or classifying) the candidate variation 104. The generation of the embeddings representing the candidate variation information 102 are further detailed in FIG. 2. The architecture of the deep-learning model is further detailed in FIG. 3.

In some embodiments, the methods and systems of the present disclosure use embeddings representing candidate variation information, such as a plurality of embeddings that include a plurality of read sequences, as input in a deep learning model that classifies the candidate variations. In some embodiments of the methods and systems, the embeddings can further comprise sequence quality information, sequence positional information, reference sequence information, and/or variation hypothesis information.

Figure 2:
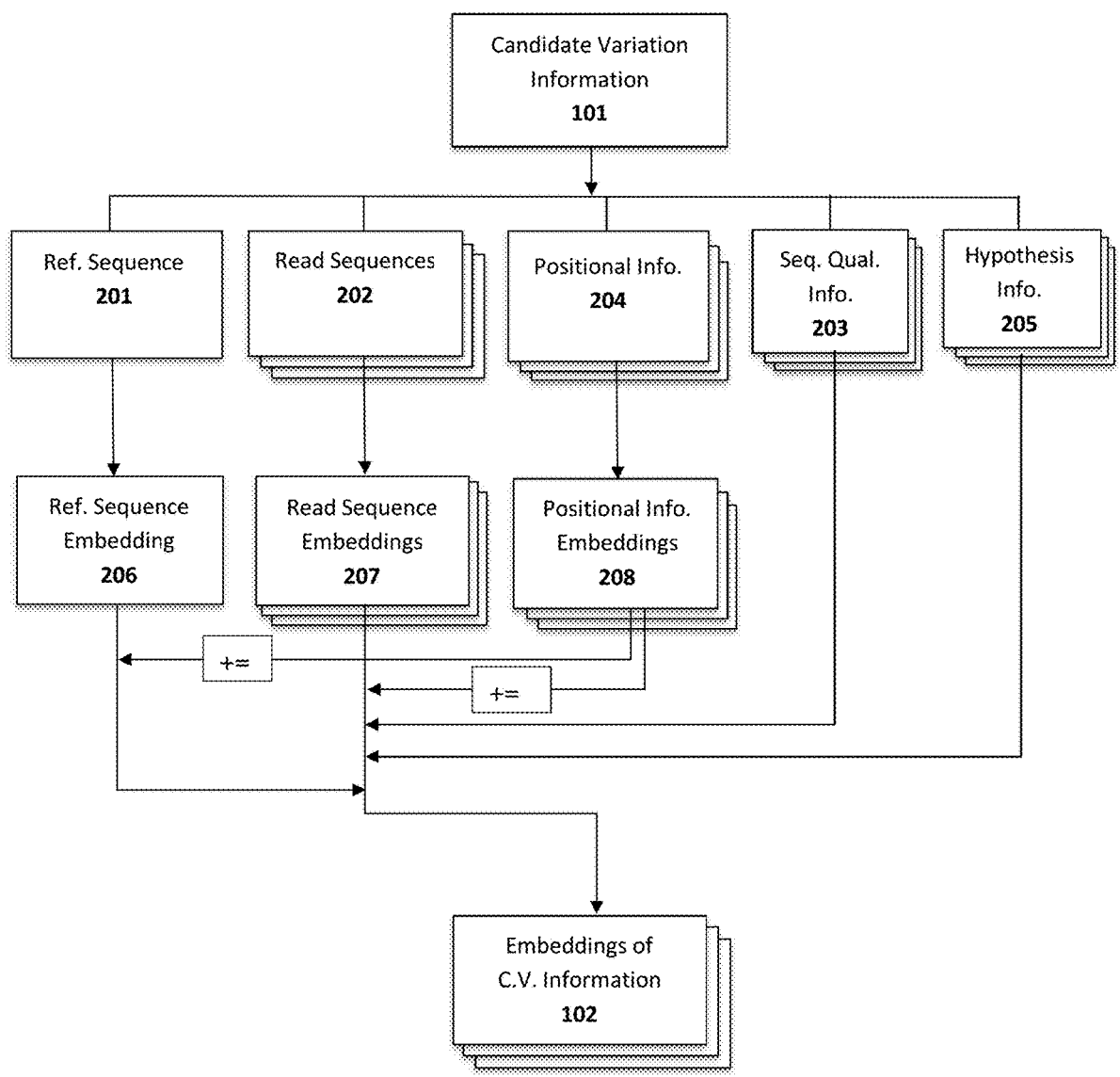
FIG. 2 depicts a block diagram of exemplary operations for use in generating embeddings of candidate variation information, including a plurality of biopolymer sequence reads, in accordance with embodiments of the present disclosure.

FIG. 2 illustrates a block diagram of exemplary candidate variation information 101 that can be extracted and used to generate embeddings of candidate variation information 102, such as embeddings of a plurality of biopolymer sequence reads. These embedding can then be processed by a deep-learning model 103 of the present disclosure as described further below. In some embodiments, the candidate variation information 102 extracted and used to generate embeddings includes a plurality of biopolymer sequence reads. In some embodiments, the candidate variation information extracted and used to generate embeddings includes a reference sequence 201, read sequences 202, quality values or scores (e.g., base quality or "BQ" values) for the read sequences 203, positional information 204 associated with the reference and read sequences, and hypothesis information 205.

In some embodiments of the methods and systems of the present disclosure, the plurality of biopolymer sequence reads are nucleic acid sequence reads. Such nucleic acid sequence reads (and corresponding reference sequences) are extracted from candidate variation information that is typically generated by a "classical" sequence analysis software tool such as GATK, and are represented as strings of bases (e.g., A, C, G, T, or U), insertions, or deletion.

In some embodiments, the plurality of sequence reads 202 correspond to those reads overlapping a location in a target or reference sequence where the site of the candidate variation is centered. Similarly, the reference sequence 201 corresponds to the sequence that encompasses the locus of the variation and the full range of the target sequence covered by the plurality of biopolymer sequence reads 202, typically an equal distance upstream and downstream of the variation site. As shown in the exemplary embodiment of FIG. 2, the embeddings of C.V. information 102 results from the concatenation of the reference sequence embedding 206 with each of the plurality of read sequence embeddings 207. As noted elsewhere herein, the concatenation of the reference sequence embedding 206 with each of the plurality of read sequence embeddings 207 results in more efficient and accurate single read processing by the deep learning model in the methods and systems of the present disclosure.

An embedding of the reference sequence 206, and embeddings of the read sequences 207 are generated as vectors of real numbers of a fixed dimension. The fixed number of dimensions of the embeddings (also sometimes referred to as "channels" of the embedding) can be selected based on factors such as desired efficiency in processing by a deep learning model. In some embodiments of the present disclosure embeddings of reference sequence 206 and read sequences 207 each comprise at least 20 dimensions. It is contemplated, however, that larger dimensions for the embeddings of the reference sequence 206 and read sequences 207 can be used in the methods and systems of the present disclosure. Accordingly, in some embodiments, the embedding of the reference sequence and/or the embeddings of read sequences comprise at least 20 dimensions, at least 50 dimensions, at least 100 dimensions, at least 200 dimensions, at least 300 dimensions, or even more.

The positional information 204 for the reference sequences 201 and the plurality of sequence reads 202 differs depending on the length and location of the read sequence relative to the candidate variation location. The location of the candidate variation can be represented by a numerical "address" or "index" that indicates the unambiguous site in a genome (or other reference sequence) where the candidate variation is centered. The sequence positional information 204 provides important information for efficient and accurate training and inference by the deep learning model 103. In order for the deep learning model to process the positional information 204 associated with the reference sequence 201 and each of the plurality of read sequences 202, embeddings representing the positional information 208 are generated. The generated embeddings of the positional information 208 have the same dimension (or number of channels) as the embeddings of the reference and read sequences (e.g., 20 dimensions). These positional information embeddings 208 are then add-assigned (as indicated by "+=" function in FIG. 2) to the embeddings of the reference sequence 206 and the embeddings of the plurality of read sequences 207. Accordingly, the positional information 204 associated with the reference sequence 201 and each read sequence 202 is effectively encoded into the embeddings of candidate variation information 102 used as input for the deep learning model. For further description of this method of positional encoding of embeddings as used in neural networks for language translation, see e.g., Vaswani, A., et al., "Attention Is All You Need," arXiv:1706.03762v5 [cs.CL] 6 Dec. 2017; nlp.seas.harvard.edu/2018/04/03/attention.html.

Accordingly, in some embodiments of the methods and systems of the present disclosure, the generating of the embeddings of the plurality of biopolymer sequence reads further comprises: generating separately an embedding of a sequence read and an embedding of sequence positional information of the sequence read and add-assigning the embedding of the sequence positional information to the embedding of the sequence read.

Sequence quality information typically is associated with the plurality of reads generated by a high throughput NGS experiment and is found in candidate variation information generated by classical sequence calling tools and algorithms. Sequence quality information can include e.g., base quality (BG) scores, and alignment quality scores. Sequence quality information typically is represented by scores which are real number scalar values (e.g., values between 0 and 100). Accordingly, such sequence quality information associated with a read sequence can easily be directly associated with an embedding of a read sequence by simply concatenating another channel to the embedding containing the scalar value of the quality information. Accordingly, in some embodiments, sequence quality information 203 is concatenated with the embeddings of the read sequence with which it is associated. For example, as shown in FIG. 2, the embeddings of C.V. information 102 can include sequence quality information 203 such as BQ values corresponding to each base of the read sequences concatenated with the embedding of each read sequence 207. For example, each BQ value is a single real number value, which can be concatenated to the embedding vector corresponding to each base. The inclusion of a BQ score for each base position in the embeddings representing the sequence reads provides an additional parameter that can contribute to accurate detection of candidate variations.

Similarly, as illustrated by FIG. 2, the concatenation of hypothesis information 205 with the candidate variation information embeddings 102 further facilitates accurate and efficient processing by the neural networks of the deep learning model 103 in detecting candidate variations. In the methods and systems for classifying candidate variations of the present disclosure, the hypothesis information 205 corresponds to an additional channel concatenated to each base of the read sequence embeddings 207 that includes a 1 or 0 indicating true or false at the base position of the read sequence for a particular sequence hypothesis. For example, for a 201 bp nucleic acid sequence read with a hypothesized variant of A changed to T at its central position 101, the hypothesis information 205 concatenated to the sequence read embedding 207 would correspond to a channel at every position containing a 0 and the channel at position 101 containing a 1. In some embodiments, the sequence hypothesis information 205 can comprise separate channels for each different type of sequence variation hypotheses, including but not limited to, single base change to an A, C, G, or T, insertion, or deletion. For example, in the case of a deletion of multiple bases from read sequence positions 97 to 100, the concatenated hypothesis information 205 would include channels at positions 97-100 containing a 1 and at all other channels a 0.

Similarly, in some embodiments, in order to facilitate training and/or inference using the deep learning model 103, additional candidate variation information 101 can be included with the reference 206 and/or read sequence embeddings 207 by further concatenation of channels encoding the additional information as a 0 or 1. For example, in some embodiments, channels are concatenated to the reference 206 and read sequence embeddings 207 that encode the start and/or stop positions, and/or the strand direction associated with the plurality of sequence reads.

In an exemplary embodiment of generating a plurality of embeddings including a plurality of biopolymer sequence reads, as depicted in FIG. 2, a dataset of candidate variation information 101 comprising 100 nucleic acid sequence reads would result in 100 embeddings of candidate variation information 102. Assuming that vectors of dimension 20 are used to represent each base, insertion, or deletion position of the plurality of read sequences in the embeddings, the resulting plurality of embeddings of candidate variation information 102 would include a vector of total dimension 41 (read base: dim 20)+(BQ value: dim 1)+(reference base: dim 20). Further, assuming that the nucleic acid read sequences are 200 positions in length, the resulting embeddings of candidate variation information 102 would comprise a 41×200 2D-array of real numbers representing each read sequence. The complete set of embeddings 102 representing the plurality of 100 sequence reads would result in a 3D array of dimensions 100×41×200, for a total 820,000 real numbers representing candidate variation information ready for processing by a deep learning model 103. Because, as described above, the embedding of the positional information 208 is add-assigned to the embeddings of sequence reads 207, the size of the 3D array is greatly reduced.

The association of the reference sequence embedding 206 with each individual sequence read embedding 207 provides additional speed and efficiency in processing the embeddings with the deep learning model 103 by allowing for abbreviated processing of candidate variation information embeddings at locations having relatively large numbers of redundant overlapping read sequences that may quickly converge at a classification. For example, if a classification can be extracted by the neural network using only 10 of a total of 25 available embeddings of candidate variation information representing 25 read sequences, then the processing of this particular candidate variation classification can be terminated 15 embeddings early and processing for the next candidate variation begun resulting in savings of computing cost and time.

The plurality of sequence reads representing each of the potentially millions of candidate variations in a typical high-throughput sequencing dataset can vary substantially, e.g., from N=10 to N=10,000. This variation in the number of reads associate with the different candidate variations that need to be classified across a large sequencing dataset creates difficulty in processing using neural networks. It is an advantage of the methods and systems of the present disclosure that the variable sized datasets of sequence reads associated with different candidate variations can be efficiently processed and classified with a deep learning model as described further below.

Generally, a deep learning model has an "architecture" or configuration that comprises a sequence of neural networks, in series and/or in parallel, that each includes a plurality of neural layers. A deep learning model can thus be described in terms of sequence of layers, the operation performed by each layer, and the connectivity between the layers. Key features of the neural network layers are the "kernels" (or "filters") that perform the computational transformations on the data input to the layer and result in the transformed output. The kernels each have associated adjustable weighting parameters and the combination of the kernels and their weights determine the exact computational transformation performed by the layer. The weighting values of the kernels are "learned" or "trained" by iterative adjustment in a minimization process using a loss function. The final learned values of the weighting parameters, which are set at the end of training, determine the architecture of the deep learning model that can be used for an inference task, such as the classification of candidate variations identified in high throughput sequencing datasets.

In some embodiments of the methods and systems of the present disclosure, the detecting of candidate variations further comprises processing the plurality of embeddings with a deep learning model wherein the model detects (or classifies) the candidate variation. In some embodiments, processing with the deep learning model further comprises: transforming the embeddings with a series of 1-dimensional convolution layers; max and mean pooling output of the series of 1-dimensional convolution layers; and transforming output of max and mean pooling with a series of fully connected layers that output the detection (or classification) of the candidate variation.

Figure 3:
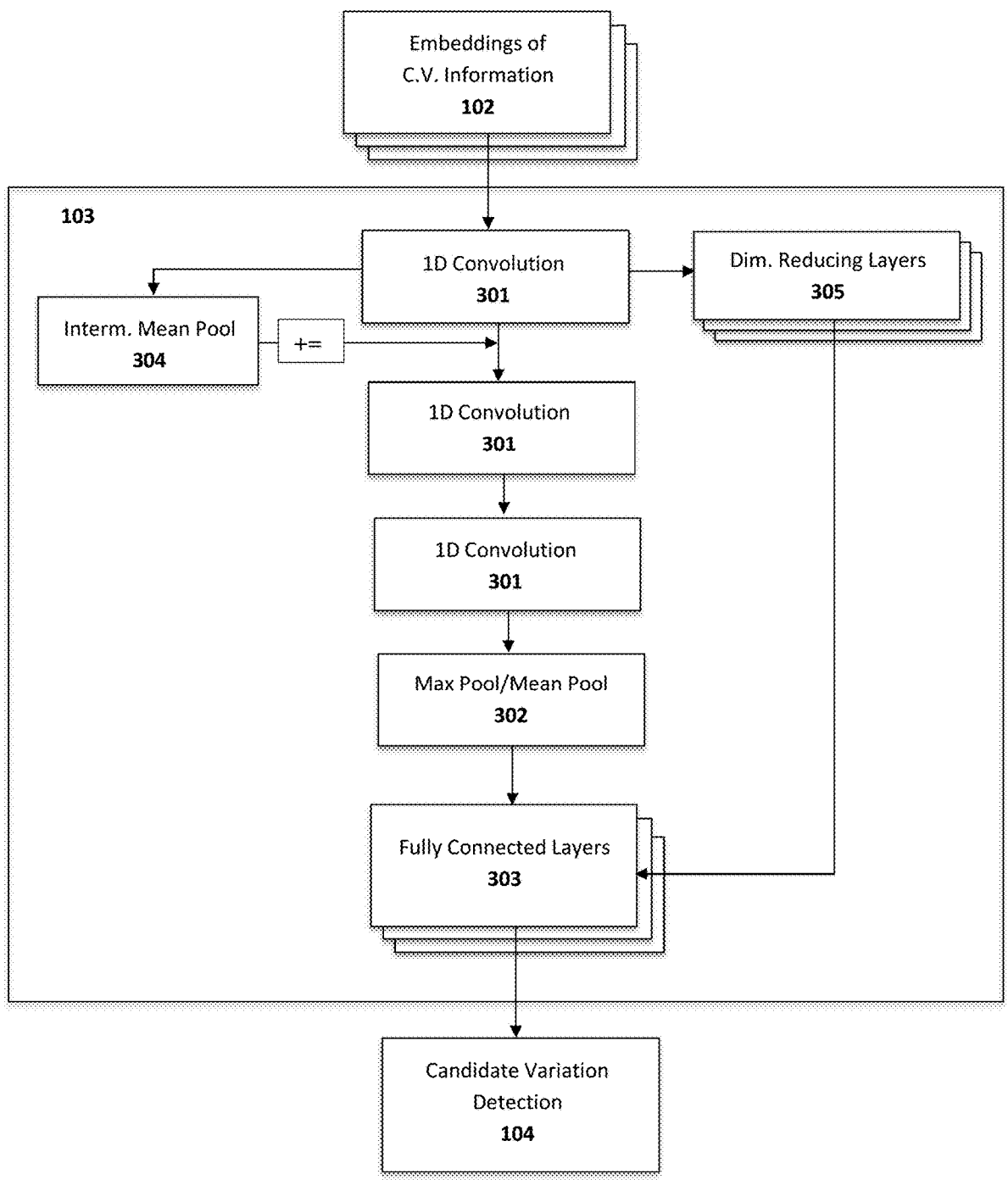
FIG. 3 depicts a block diagram of an exemplary deep learning model architecture useful for processing embeddings of candidate variation information including biopolymer sequence reads in accordance with embodiments of the present disclosure.

FIG. 3 depicts a block diagram illustrating an exemplary architecture of a deep learning model 103 useful for processing embeddings of candidate variation information 102, including a plurality of biopolymer read sequences, and detecting a candidate variation classification 104. In some embodiments, the deep learning model is configured to carry out at least the following: (1) transform the embeddings with a sequence of 1D convolution layers 301, wherein the 1D convolution layers do not combine information between different read sequences; (2) transform output of the sequence of 1D convolution layers with a Max Pool/Mean Pool layer 302, wherein the Max Pool/Mean pool layer performs max pooling and mean pooling that combines information between different read sequences; and (3) transform the output of the Max Pool/Mean Pool layer 302 with a sequence of fully connected layers 303, wherein the output of the fully connected layers 303 is the detection of the candidate variation 104.

FIG. 3 depicts an exemplary sequence of three 1-dimensional (or "1D") convolution layers 301 (also referred to herein as "Conv1D layers"), in some embodiments of the deep learning model, the number of 1D convolution layers can be 3, 4, 5, 6, 10, 25, 50, or greater. The 1-dimensional convolution layers perform a 1D convolution of the input embeddings of candidate variations 102. This 1-dimensional convolution results in sharing of information between the different embedding channels of a read sequence, the 1-dimensional convolution does not combine (or share) information between different read sequences. That is, the transformation carried out by the 1-dimensional convolution layers maintains information from the different individual embeddings representing different sequence reads separately. This use of Conv1D layers that do not share information from different sequence reads is distinctly different than the use of 2D convolutional layers to extract features from pileup image of read sequences as in the DeepVariant model. The use of 1D convolutional processing in the deep learning model of the present disclosure does not require maintaining a specific order of read sequences and allows for real-time, single-read processing. As noted elsewhere herein, the real-time, single-read processing can provide more efficient deep learning processing of the variable-sized sets of read sequences associated with each of the potentially millions of variation candidates in an NGS dataset.

Generally, in the methods of the present disclosure stack of 1D convolutional layers can be used, wherein the layers have relatively small kernel sizes. It is contemplated, however, that dilation methods can be used to expand kernel size. In some embodiments, 1D convolution layers have a kernel size of at least 3 (or a kernel dimension of at least 3×1). It is contemplated that in some embodiments, particularly with read sequence embeddings of larger than 20 dimensions, that kernel sizes larger than 3 can be used. Accordingly, in some embodiments the 1D convolution layers have a kernel size of at least 3, at least 5, at least 8, at least 10, at least 15, at least 30, or even more.

For example, as depicted in FIG. 3, the output of the sequence of 1D convolution layers 301 is subsequently processed by a layer 302 (or layers) that performs max pooling ("MaxPool") and mean pooling ("MeanPool"). The MaxPool/MeanPool layer 302 combines information between different individual sequence reads of the plurality of biopolymer sequence reads. The output of layer 302 is a dimensionally reduced array of values averaged and maxed across the plurality of embeddings of different sequence reads, that is input to a sequence of fully connected layers 303. These fully connected layers 303 transform the input of embeddings of candidate variation information 102 processed by the preceding sequence of layers and output detection of the candidate variation 104.

The output detection of the candidate variation 104 can include an output value, that based on whether it meets some predetermined threshold, confirms whether a true variation has been observed at a specific location relative to a reference sequence. Additionally, as noted elsewhere herein, the detection of the candidate variation can provide further information, such as the type of variation (e.g., insertion, deletion, SNP), and/or whether the variation occurs on more than one allele of a genome. Thus, in some embodiments, the detection of the candidate variations provide not just confirmation that a candidate variation is a true sequence variant but also, for example, a determination of whether it is heterozygous or homozygous.

As noted above, post-sequencing processing high-throughput sequencing datasets using classical variant calling tools (e.g., GATK) can potentially identify millions of candidate variations, each at different genomic location, each having different number of associated sequence reads, and each read with different characteristics of mapping quality, and/or base quality. The large number and differing characteristics of each candidate variation in a dataset makes accurate and efficient classification using deep learning very difficult to achieve. Accordingly, in some embodiments, the exemplary architecture of the deep learning model 103 depicted in FIG. 3 includes additional optional features that provide further accuracy and efficiency in classifying candidate variation information.

In some embodiments of the methods comprising processing with a deep learning model, the method further comprises: mean pooling output from at least one of the series of 1-dimensional convolution layers and adding back the mean pooling values into the input of the subsequent 1-dimensional convolution layer. For example, as depicted in FIG. 3, in some embodiments, the deep learning model 103 is further configured to transform output from at least one of the sequence of 1-dimensional convolution layers 301 with an intermediate mean pooling layer 304 (or "intermediate Mean Pool layer") and add back the mean pooling values of this intermediate layer into the input of the next in the sequence of 1-dimensional convolution layers 301. This optional intermediate mean pooling layer 304 combines information between different read sequences to in generating the mean values. By adding back these mean values from across different read sequences to the output from the 1-dimensional convolution layer, that does not combine information across different read sequences, the intermediate Mean Pool layer 304 effectively allows the neural network to learn early on in processing of the embeddings from a "consensus" values across all reads. This use of the intermediate Mean Pool 304 in the deep learning model enhances processing efficiency and can allow early detection of anomalies in the read sequences of the candidate variation information.

Although depicted in FIG. 3 as a single layer accepting input from the first 1-dimensional convolution layer 301, it is contemplated that in some embodiments the intermediate mean pooling can be carried out between later 1-dimensional convolution layers in the sequence. Furthermore, in some embodiments, it is contemplated that more than one intermediate Mean Pool layer 304 can be used between the sequence of 1-dimensional convolution layers 301. In some embodiments, the deep learning model can be configured with an intermediate Mean Pool layer 304 located between every pair of 1-dimensional convolution layers in the sequence.

In some embodiments of the deep learning model 103, it is contemplated that the processing of the embeddings of candidate variation information 102 is carried out wherein the embeddings are processed in parallel, that is processed directly through the sequence of 1-dimensional convolution layers 301 while bypassing any intermediate Mean Pool layers 304, and also processed through the intermediate Mean Pool layers 304. In such a parallel processing embodiment, a comparative analysis of the processing with or without the intermediate Mean Pool for the single reads can be carried out to identify potentially anomalous reads in the dataset. Accordingly, in some embodiments, the anomalous reads identified early using the intermediate Mean Pool layer would be eliminated from further processing of the dataset by the deep learning model.

In some embodiments of the methods comprising processing with a deep learning model, the method further comprises: transforming output from at least one of the series of 1-dimensional convolution layers with a series of dimension-reducing layers that output directly into the fully connected layers. For example, as depicted in FIG. 3, in some embodiments, the deep learning model 103 is further configured such that at least one of the sequence of 1-dimensional convolution layers 301 outputs to a "highway" of dimension-reducing layers 305 that bypass the max and mean pooling 302 and output directly to the fully connected layers 303. This dimension reducing layers 305 are able to take output of a 1-dimensional convolution layer 301 which corresponds to a single read sequence embedding and reduce the dimensionality of the embedding such that it can processed by the fully connected layers 303. This direct processing by the fully connected layers prevents mixing between different individual read sequences. This processing "highway" in the deep learning model results in increased processing efficiency where the candidate variation dataset is already very good. For example, a candidate variation site that has many overlapping read sequences with little or no variance between them. Additionally, because it bypasses the Mean Pool/Max Pool layer, the bottleneck layer "highway" maintains the order of the reads as they are processed. This order information for the read sequence processing can be useful in further analysis or treatments of the dataset.

As noted above, direct input into the fully connected layers 303 requires transformations that result in large reductions in dimensionality. Accordingly, in some embodiments, the dimension-reducing layers 305 can comprise a "bottleneck" layer followed by a linear mapping layer that takes the 2D tensor output of an embedding and convert it to a single small vector. For example, in one embodiment, the dimension-reducing layers 305 accept input of an exemplary 201×41 tensor corresponding to an embedding of candidate variation information comprising a single read and transforms to a single vector of dimension of 32. This single vector output of the dimension reducing layers 305 then bypasses the Max Pool/Mean Pool layer 302 and inputs directly into the fully connected layers 303.

As with the optional intermediate Mean Pool layer, in some embodiments of the deep learning model 103, it is contemplated that the processing of the embeddings of candidate variation information 102 by the "highway" of the dimension-reducing layers 305 is carried out in parallel with processing of the same information directly through the series of 1-dimensional convolution layers 301 and subsequent Max/Mean pooling 302. In such a parallel processing embodiment, an analysis of the single read information processed through the highway of the bottleneck layer can rapidly identify sets of read sequences that are already low in errors and amenable to classification without the processing by the full sequence of 1-dimensional convolution layers and Mean/Max pooling. This parallel early classification of good candidate variation information thereby provides to the overall efficiency of the deep learning model.

It is a surprising technical effect and advantage of the deep learning model architecture illustrated in FIG. 3 that processing embeddings of candidate variation information though plurality of 1-dimensional convolution layers, a Mean Pool/Max Pool layer, in parallel with an intermediate Mean Pool layer and/or a bottleneck layer, provides accurate and efficient classification of candidate variations. Moreover, the advantages of this deep learning model that efficient and accurate classification can be achieved even when starting with suboptimal (e.g., low-coverage) sequencing datasets (e.g., average coverage less than 30×, less than 20×, less than 15×, or less than 10×).

As described above, prior to using the deep learning model for an inference task, such as the classification candidate variations, a training process is carried out in which the neural networks of the model "learn" an optimal set of parameters (e.g., adjustable weighting factors) that result in the best fit of a training dataset (e.g., a suboptimal sequencing dataset) to a model reference dataset (e.g., a standard reference genome sequence). This learning process typically involves an iterative stochastic gradient descent-based minimization through the space of neural network adjustable weighting factors. The training process thus typically includes error calculation and then back-propagation of the error through the network to adjust the weighting parameters.

The training of a deep learning model to classify candidate variations, as contemplated herein, can include both the more time-consuming initial training of a model, and also include the less time-consuming "transfer learning" training of a model. Transfer learning is carried out on a previously trained neural network and simply re-trains it using data that differs in some respect from the training data originally used to train the neural network. Accordingly, in transfer learning the adjustments made to the kernel weighting parameters are typically more limited than in the initial training. In transfer training selected weights and/or selected kernels can be held constant, while others are adjusted. In this way, transfer learning can train the neural network to work better in classifying different types of datasets without carrying out a complete re-training of the neural networks.

In some embodiments of the methods and systems of the present disclosure, transfer learning can be carried out by training a neural network of a deep learning model that has already been initially trained on embeddings of a suboptimal dataset. In such embodiments, the transfer learning process typically is carried out using embeddings of a new and/or slightly different type of high-throughput sequencing dataset. For example, a deep learning model initially trained using embeddings of candidate variation information, including a plurality of biopolymer sequence reads, from one type of sequencing instrument could be re-trained, at least partially, with embeddings of information obtained from different type of instrument. Thus, the learning from the initial training on the first type of sequencing instrument would be transferred in the training of the neural network with embeddings of sequencing data from the second type of instrument. Because it does not require starting over from scratch in determining the weighting parameters, the training process involved in transfer learning is greatly reduced. Accordingly, it is contemplated in the methods of the present disclosure for detecting candidate variations based on embeddings of candidate variation information, including sequence reads, that the method further comprises training of the deep learning model. In some embodiments, the further training corresponds to transfer learning using embeddings of candidate variation information and embeddings of model sequencing data from a different type of sample, sequencing instruments, and/or candidate variation calling software than was used in the original training of the deep learning model.

In some embodiments of the methods and systems of the present disclosure comprising training the deep learning model, the training comprises: generating a plurality of embeddings of suboptimal candidate variation information, wherein the information comprises a plurality of sequence reads, and a model reference sequence; processing the embeddings with a deep learning model that detects the suboptimal candidate variation; and minimizing error in the detection of the suboptimal candidate variation relative to a ground truth candidate variation of the model reference sequence by adjusting parameters of the deep learning model.

In some embodiments of the methods and systems comprising training the embeddings further comprise suboptimal candidate variation information including a read sequence, a model reference sequence, and positional information for the read and model reference sequences.

In some embodiments of the methods and systems of the present disclosure comprising training the deep learning model, the processing of embeddings further comprises: transforming the embeddings with a series of 1-dimensional convolution layers; max and mean pooling output of the series of 1-dimensional convolution layers; and transforming output of max and mean pooling with a series of fully connected layers that output detection of the suboptimal candidate variation. In some embodiments of the methods and systems comprising training, the processing of the embeddings further comprises: mean pooling output from at least one of the series of 1-dimensional convolution layers and adding back the mean pooling values into the input of the subsequent 1-dimensional convolution layer. Additionally, in some embodiments of the methods and systems comprising training, the processing of the embeddings further comprises: transforming output from at least one of the series of 1-dimensional convolution layers with a series of dimension-reducing layers that output directly into the fully connected layers.

The various methods of present disclosure can also be embodied in a system. It is contemplated that any of the embodiments of the methods, and the various features useful in the methods for generating embeddings of a plurality of biopolymer sequence read and using them to detect candidate variations as described throughout, can be incorporated as features in the non-transitory computer-readable medium. Accordingly, in some embodiments, the present disclosure provides a system comprising a processor, a memory device, and a classification engine executable on the processor according to software instructions stored in the memory device, wherein the classification engine is configured to: generate a plurality of embeddings including a plurality of biopolymer sequence reads; and detect one or more candidate variations in the sequence reads based at least in part on the plurality of embeddings. In some embodiments of the system, the system is configured to process the embeddings with a deep learning model, and in some embodiments of the system the deep learning model is configured to: transform the embeddings with a series of 1-dimensional convolution layers; max and mean pool output of the series of 1-dimensional convolution layers; and transform output of max and mean pooling with a series of fully connected layers that outputs detection of the candidate variation. Additionally, in some embodiments of the system, the deep learning model can be configured to: mean pool output from at least one of the series of 1-dimensional convolution layers and adding back the mean pooling values into the input of the subsequent 1-dimensional convolution layer; and/or configured to transform output from at least one of the series of 1-dimensional convolution layers with a series of dimension-reducing layers that output directly into the fully connected layers.

In some embodiments the system can further comprise a training engine executable on the processor according to software instructions stored in the memory device, wherein the training engine is configured to: generate a plurality of embeddings of suboptimal candidate variation information, wherein the information comprises a plurality of sequence reads, and an embedding of a model reference sequence; process the embeddings with a deep learning model that detects the suboptimal candidate variation; and minimize error in the detection of the suboptimal candidate variation relative to a ground truth candidate variation of the model reference sequence by adjusting parameters of the deep learning model.

Figure 4:
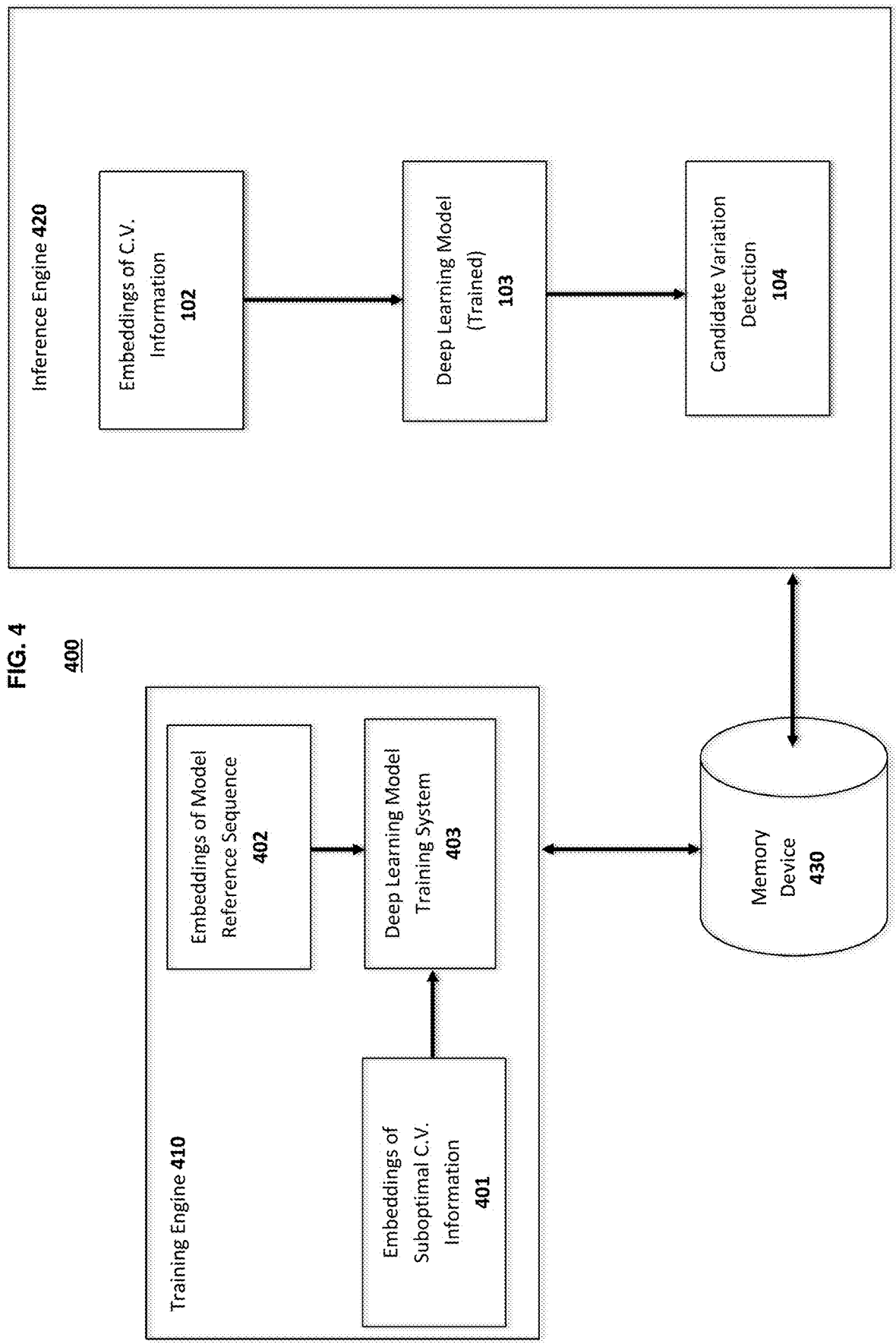
FIG. 4 depicts a block diagram of an exemplary system useful for detecting candidate variations in embeddings of sequencing data using a deep learning model, as well as, training the deep learning model, in accordance with embodiments of the present disclosure.

FIG. 4 illustrates an exemplary system and flow of operations for training and then using a trained deep learning model to detect candidate variations. Embeddings of suboptimal candidate variation information 401, including a plurality of biopolymer sequence reads, and embeddings of model reference sequence data 402 are generated and input into a deep learning model training system 403. In order to train the deep learning model to detect variations from suboptimal (e.g., low coverage) sequencing data, the model reference sequence used in the training should be include the ground truth candidate variations for the relevant locations in the sequence where candidate variations are identified. Typically, the model reference sequence is a fully-characterized sequence that has been determined using high-coverage sequencing dataset and confirmed by independently conducted experiments, such that it provides the true position and identity of every monomer unit (e.g., base pair) of the sequence to an accepted degree of confidence. The embeddings of the model reference sequence 402 can thereby be used as the "ground truth" set for training the deep learning model.

In some embodiments, the model reference sequences useful in the training methods are obtained from high-quality (e.g., 30× or greater coverage) sequencing datasets wherein the true sequence at each location has been confirmed by repeated experiments. Such high-quality sequences useful as a model reference sequence for training can be prepared by carrying out high-quality NGS experiments and analysis on well-known samples. In some embodiments, the model reference sequence can be a "gold-standard" genome sequence from a source such as the publicly available benchmark human genomes available from the "Genome in a Bottle Consortium" (available at: jimb.stanford.edu/giab) or the mouse genome from the "Mouse Genome Project" (available at: www.broadinstitute.org/mouse/mouse-genome-project).

Generally, the suboptimal candidate information is obtained, as described elsewhere herein, from low-coverage sequencing datasets, whether experimentally obtained or simulated, using standard software tools for generating candidate variations, such as GATK. The suboptimal candidate variation information can be obtained from sequencing datasets that are of a lower quality in some respect relative to the sequencing data used for the model reference sequence. For example, whereas a model reference sequence typically will be generated from a sequencing dataset obtained with an average of 30× or greater read sequence coverage across the full sequence, the suboptimal candidate variation information will be generated from a sequencing dataset obtained with an average of less than 30×, less than 20×, less than 15×, less than 12×, or even less than 10× sequence read coverage.

The ultimate accuracy of the trained deep learning model depends at least in part on the quality level of the model reference sequence. In some embodiments, for training, the model reference sequence and the suboptimal candidate variation information are obtained from the same experiment or using the same experimental conditions. In some embodiments, the suboptimal candidate variation information can be prepared from the model reference sequence sequencing data by excluding some portion of the dataset, such as some portion of the plurality of read sequences, thereby creating effectively a low-quality dataset. For example, by randomly excluding half of the sequence reads from a high-quality 30× coverage NGS dataset, it can be effectively down-graded to a suboptimal, 15× coverage dataset. Other methods known in the art for simulating low-quality data from high-quality dataset e.g., by introducing noise can also be used.

As shown in FIG. 4, embeddings of the suboptimal candidate variation information 401 are used together with embeddings of model reference sequences 402 as input to a deep learning model training system 403. The embeddings of the suboptimal and model data used in training are generated using the same methods described elsewhere herein for embeddings (see e.g., FIG. 2 and description). The training system 403 is configured for training the deep learning model to accurately detect candidate variations identified in the suboptimal sequencing dataset. The general training process uses the embeddings of the suboptimal candidate variation information 401, which includes a plurality of biopolymer sequence reads, and the embeddings of the model reference sequence 402 as input to a deep learning model training system 403 which comprises an untrained version of the deep learning model architecture. Then an initial output of detection of the candidate variation from the untrained model is obtained and the error of this initial detection (or classification) of the candidate variation is determined relative to the ground truth candidate variation classification of the model reference sequence. In some embodiments, the error determination is carried out using a loss function, or similar type of calculation that quantifies the error between the detection of the suboptimal candidate variation and the ground-truth candidate variation known from the model reference sequence.

Training is carried out as an iterative process whereby the error of each iteration is used to adjust the model parameters, and when the error calculated at the end of an iteration drops below some threshold, the error is determined to be minimized and the deep learning model is considered "trained" or "optimized" for use in the inference engine 420. Accordingly, the training process comprises minimizing error in the classification of the suboptimal candidate variation relative to a ground truth candidate variation of the model reference sequence by adjusting parameters of the deep learning model.

In some embodiments, the minimizing the error is carried out through a stochastic gradient descent involving iterative adjustment of weighting parameters within the deep learning model that produces a trained deep learning model 103. A range of loss functions useful in training neural networks, such as CNNs, are known in the art and can be used in the candidate variation classifying methods and systems of the present disclosure.

The computations and data manipulations carried out within the deep learning model for classifying candidate variations from sequencing data are beyond the capabilities of a human. The training and use of the neural networks generally require high-performance, energy efficient computer processors and is often carried out using graphics processing units (GPUs) or farms of GPUs. Accordingly, in some embodiments, the present disclosure provides a computing device configured to apply the deep learning model in a process for candidate variation classification from the vast quantities of digital data associated with a genome sequence.

FIG. 4 further illustrates a block diagram 400 of an exemplary computer-based system useful for training and using the trained neural network system to classify candidate variations from obtained sequencing datasets in accordance with embodiments of the present disclosure. The primary computer-based elements include a training engine 410 and an inference engine 420. As described above, the training engine is configured to accept input of embeddings of suboptimal candidate variation information 401 and embeddings of a model reference sequence 402 and is connected to a memory device 430, which can comprise temporary memory and/or a persistent storage device. The training engine 410 carries out the computer-based instructions for configuring the neural networks of the deep learning model training system 403 based upon the training process. The deep learning model parameters during training can be stored in the memory device 430. The primary function of the training engine 410 in concert with the memory device 430 is to train and provide the final trained deep learning model that can be accessed and used by the inference engine 420 for the detection (or classification) of candidate variations.

The computer-based implementation of the inference engine 420 is configured to accept input of the embeddings of candidate variation information 102, which information includes a plurality of biopolymer sequence reads, and processing it using the trained deep learning model 103 that ultimately outputs the detection of a candidate variation 104. The input of the embeddings information 102 and the output of the candidate variation detection result 104 can be stored in the memory device 430.

It is contemplated that in some embodiments the inference engine 420 can provide further computer-based treatment prior to the input such as generating embeddings of the candidate variation information based on information obtained from other software tools (e.g., GATK or SAMtools). It is also contemplated that the inference engine can provide further treatment of the candidate variation detection (or classification) output, such as, reassembling the classified variant sequence to provide as output full-length sequence comprising the variations based on the complete reference sequence.

The various computer-based elements illustrated in FIG. 4, and the functions attributed to them, are described generally for ease of understanding. One skilled in the art will recognize that one or more of the functions ascribed to the various elements may be performed by any one of the other elements, and/or by an element not shown in the figure. Furthermore, it is contemplated that the elements may be configured to perform a combination of the various functions described above as supported by the various embodiments described elsewhere herein. Accordingly, the description of a training engine 410, an inference engine 420, a and a memory device 430 are intended to include any suitable combination of computing devices, including servers, interfaces, systems, databases, agents, peers, engines, controllers, modules, or other types of computing devices operating individually or collectively to perform the functions ascribed to the various elements. Further, one skilled in the art will recognize that one or more of the functions of the system of FIG. 4 described herein may be performed within the context of a client-server relationship, such as by one or more servers, one or more client devices (e.g., one or more user devices) and/or by a combination of one or more servers and client devices.

Figure 5:
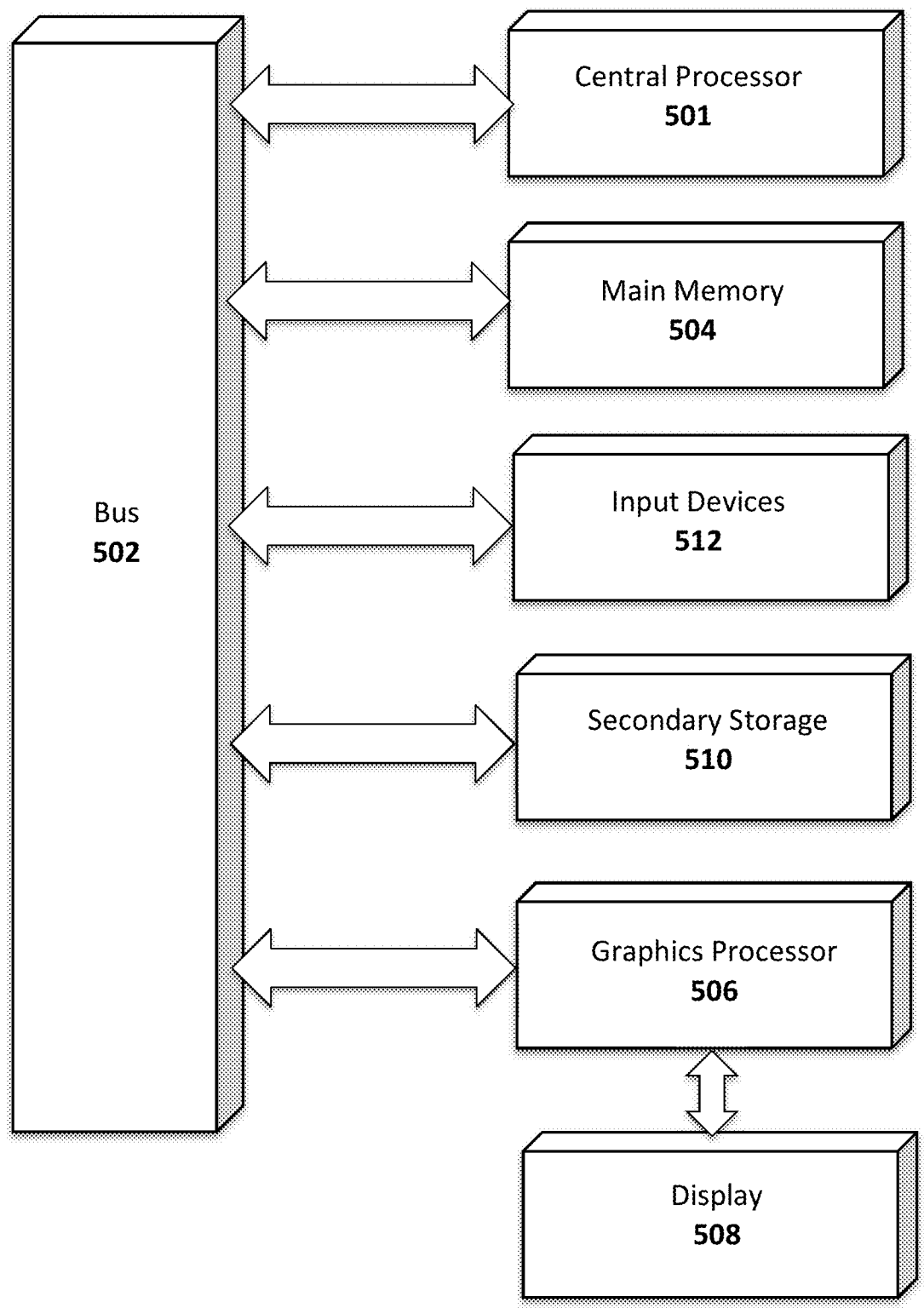
FIG. 5 depicts a system in which the processes, architecture, and/or functionality useful for detecting candidate variations in embeddings of sequencing data using a deep learning model in accordance with embodiments of the present disclosure may be implemented.

FIG. 5 depicts an exemplary system 500 in which the embodiments of the general candidate variation detection process 100, the generation of embeddings of candidate variation information 200, the deep learning model architecture 300, and/or the training engine and inference engine functionalities 400 may be implemented. The system 500 includes at least one central processor 501 connected to a communication bus 502. The communication bus 502 may be implemented using any suitable protocol, such as PCI (Peripheral Component Interconnect), PCI-Express, AGP (Accelerated Graphics Port), HyperTransport, or any other bus or point-to-point communication protocol. The system 500 also includes a main memory 504. Control logic (software) and data are stored in the main memory 504 which may include random access memory (RAM). The system 500 also includes input devices 512, a graphics processor 506, and a display 508, such as a conventional CRT (cathode ray tube), LCD (liquid crystal display), LED (light emitting diode) display, and the like. User input may be received from the input devices 512, which can include, but is not limited to, keyboard, mouse, touchpad, microphone, and the like. In one embodiment, the graphics processor 506 may include a plurality of shader modules, a rasterization module, etc. Each of the foregoing modules may even be situated on a single semiconductor platform to form a graphics processing unit (GPU). As used herein, a single semiconductor platform may refer to a sole unitary semiconductor-based integrated circuit or chip, or to multi-chip modules with increased connectivity which simulate on-chip operation. The various modules may also be situated separately or in various combinations of semiconductor platforms per the desires of the user. The system 500 may also include a secondary storage 510, for example, a hard disk drive and/or a removable storage drive, representing a floppy disk drive, a magnetic tape drive, a compact disk drive, digital versatile disk (DVD) drive, recording device, universal serial bus (USB) flash memory.

Software instructions, computer programs, and/or computer control logic algorithms, may be stored in the system's main memory 504 and/or the secondary storage 510. Such software instructions, when executed, allow the system 500 to perform various functions. The main memory 504, secondary storage 510, and/or any other storage are examples of computer-readable media.

In one embodiment, the functionality and/or architecture of the various previous FIGS. 1-4 may be implemented in the context of the central processor 501, the graphics processor 506, an integrated circuit (not shown) that is capable of at least a portion of the capabilities of both the central processor 501 and the graphics processor 506, a chipset (i.e., a group of integrated circuits designed to work and sold as a unit for performing related functions, etc.), and/or any other integrated circuit.

In some embodiments, the functionality and/or architecture of FIGS. 1-4 may be implemented in the context of a general computer system, a circuit board system, an application-specific system, and/or any other desired system. For example, the system 500 may take the form of a desktop computer, laptop computer, server, workstation, embedded system, and/or any other type of logic. In some embodiments, the system 500 may take the form of various other devices including, but not limited to a personal digital assistant (PDA) device, a mobile phone device, a television, etc.

It is also contemplated, that in some embodiments, the system 500 may be coupled to a network (e.g., a telecommunications network, local area network (LAN), wireless network, wide area network (WAN) such as the internet, peer-to-peer network, cable network, or the like) for communication purposes.

In some embodiments, the methods and systems of classifying candidate variations using deep learning as described in the present disclosure and exemplified by FIGS. 1-4, may be implemented, controlled, and/or otherwise utilized remotely via the internet, or other network system. For example, the system 500 could be hosted on one or more servers that could be accessed by remote users and used to classify candidate variations from the users sequencing datasets. Accordingly, in some embodiments, users can upload their own sequencing datasets and/or candidate variation information for classification using a fully trained version of the deep learning model 103 hosted on a server.

Additionally, in some embodiments users can also upload their own suboptimal sequencing datasets and/or suboptimal candidate variations for further training of the deep learning model (e.g., reference learning) hosted on the remote servers. The user would then use the further trained deep learning model hosted on the servers to classify the candidate variations generated by their own sequencing datasets. Typically, users would download the output variation classifications for further use locally, however in some embodiments the hosted system for variation classification could include other tools for analysis such as databases of model or suboptimal candidate variation information, model reference sequences, and/or other data useful in various methods of sequence analysis described herein.

Generally, the computing devices useful with the deep learning-based variation detection and classification processes and systems of the present disclosure can include any suitable combination of computing devices, including servers, interfaces, systems, databases, agents, peers, engines, controllers, modules, or other types of computing devices operating individually or collectively. At least one processor (e.g., GPU, CPU, ASIC, FPGA, DSP, x86, ARM, etc.) of the computing device is configured (or programmed) to execute software instructions stored on a computer readable tangible, non-transitory medium (e.g., hard drive, solid state drive, RAM, flash, ROM, etc.) and thereby carry out the processes involved in the methods of training and employing the deep learning model for classifying variations.

In the various embodiments of the non-transitory computer-readable medium, the various features useful in the methods and systems for classifying candidate variations described elsewhere herein, including inter alia, the use of embeddings, the deep learning model used to process the embeddings, and the methods of training (including transfer learning), can also be incorporated as features in the non-transitory computer-readable medium.

Accordingly, in some embodiments the present disclosure provides a non-transitory computer-readable medium comprising instructions for detecting candidate variations that, when executed by a processor, cause the processor to perform one or more steps comprising: generating a plurality of embeddings including a plurality of biopolymer sequence reads; and detecting one or more candidate variations in the sequence reads based at least in part on the plurality of embeddings. In some embodiments of the non-transitory computer-readable medium, the embeddings further comprise sequence quality information, sequence positional information, reference sequence information, and/or variation hypothesis information. In some embodiments of the non-transitory computer-readable medium, detecting comprises processing the embeddings with a deep learning model, and in some embodiments, processing the embeddings with a deep learning model comprises: transforming the embeddings with a series of 1-dimensional convolution layers; max and mean pooling output of the series of 1-dimensional convolution layers; and transforming output of max and mean pooling with a series of fully connected layers that output detection of the candidate variation. Additionally, in some embodiments of the non-transitory computer-readable medium, processing the embeddings with a deep learning model further comprises: mean pooling output from at least one of the series of 1-dimensional convolution layers and adding back the mean pooling values into the input of the subsequent 1-dimensional convolution layer. In some embodiments of the non-transitory computer-readable medium, processing the embeddings with a deep learning model further comprises: transforming output from at least one of the series of 1-dimensional convolution layers with a series of dimension-reducing layers that output directly into the fully connected layers.

The software instructions to configure or program the computing devices to provide the candidate variation classification functionality can be prepared using standard programming tools. For example, the extraction and generation of embeddings of candidate variation information from high-throughput sequencing data can be programmed using the specifications of the VCF and BAM file formats and software tools available online e.g., SAMtools repository at github.com/samtools. Deep learning model architecture and the neural network configurations can be programmed with the software tools such as Keras (v.2.1.3) and Tensorflow (v.1.4.0). Generally, the software instructions are embodied as a computer program product comprising a non-transitory, tangible computer readable medium storing the instructions that cause a processor of the computing device to execute the steps of the denoising processes disclosed herein.

Additionally, the methods of the present disclosure can be carried out using standard protocols and algorithms for data exchange between servers, systems, databases, or interfaces in implementing the processes. For example, data exchange used in implementing the methods and systems of the present disclosure can be conducted over a packet-switched network, a circuit-switched network, the internet, LAN, WAN, VPN (or other type of networks) using protocols based on HTTP, HTTPS, AES, public-private key exchanges, web service APIs, financial transaction protocols, or other electronic information exchange methods.

While the foregoing disclosure of the present invention has been described in some detail by way of example and illustration for purposes of clarity and understanding, this disclosure including the examples, descriptions, and embodiments described herein are intended to be exemplary, and should not be construed as limiting the present disclosure. Additional embodiments of the present disclosure are set forth in the following claims.

It will also be clear to one skilled in the art that various modifications or changes to the examples, descriptions, and embodiments described herein can be made and are to be included within the scope of this disclosure and the appended claims. Further, one of skill in the art will recognize a number of equivalent methods and procedures to those described herein. All such equivalents are to be understood to be within the scope of the present disclosure and are covered by the appended claims.

What is claimed is:

1. A computer-implemented method for detecting variations in a biopolymer sequence relative to a reference sequence comprising:

generating embeddings of at least one million sequence reads obtained by sequencing a sample of the biopolymer at less than 10× coverage, each read corresponding to a region of at least 200 bp of biopolymer sequence, wherein each embedding of a sequence read is concatenated with an embedding of a corresponding reference sequence; and detecting one or more candidate variations in the biopolymer sequence based at least in part on the embeddings of the at least one million sequence reads, wherein detecting comprises processing the embeddings with a deep learning model comprising a series of 1-dimensional convolution layers, wherein a mean pooling of one or more outputs from at least one of the 1-dimensional convolution layers is added back to the one or more outputs from the same at least one 1-dimensional layers before it is input into the subsequent 1-dimensional convolution layer, and max and mean pooling the output of the series of 1-dimensional convolution layers.

2. The method of claim 1, wherein the embeddings further comprise sequence quality information, sequence positional information, and/or variation hypothesis information.

3. The method of claim 1, wherein the method further comprises:

transforming one or more outputs from at least one of the series of 1-dimensional convolution layers with a series of dimension-reducing layers that output directly into the fully connected layers.

4. The method of claim 1, wherein the method comprises training the deep learning model, wherein training comprises:

generating a plurality of embeddings of suboptimal candidate variation information, wherein the information comprises a plurality of sequence reads, and an embedding of a model reference sequence;

processing the embeddings of suboptimal candidate variation information with a deep learning model that detects the suboptimal candidate variation; and minimizing error in the detection of the suboptimal candidate variation relative to a ground truth candidate variation of the model reference sequence by adjusting parameters of the deep learning model.

5. The method of claim 4, wherein processing the embeddings of suboptimal candidate variation information comprises:

transforming the embeddings of suboptimal candidate variation information with a series of 1-dimensional convolution layers;

max and mean pooling the output of the series of 1-dimensional convolution layers; and transforming the output of the max and mean pooling with a series of fully connected layers that output detection of the suboptimal candidate variation.

6. A system for detecting a variation in a biopolymer sequence relative to a reference sequence comprising a processor, a memory device, and a classification engine executable on the processor according to software instructions stored in the memory device, wherein the classification engine is configured to:

detect one or more candidate variations in at least one million sequence reads obtained by sequencing a sample of the biopolymer at less than 10× coverage, each read corresponding to a region of at least 200 bp of the biopolymer sequence, based at least in part on embeddings of the at least one million sequence reads, wherein each embedding of a sequence read is concatenated with an embedding of the corresponding reference sequence, and wherein detecting comprises processing the embeddings with a deep learning model comprising a series of 1-dimensional convolution layers, wherein a mean pooling of one or more outputs from at least one of the 1-dimensional convolution layers is added back to the one or more outputs from the same at least one 1-dimensional layers before it is input into the subsequent 1-dimensional convolution layer, and max and mean pooling the output of the series of 1-dimensional convolution layers.

7. The system of claim 6, wherein the embeddings further comprise sequence quality information, sequence positional information, and/or variation hypothesis information.

8. The system of claim 6, wherein the deep learning model is configured to:
  transform the one or more outputs from at least one of the series of 1-dimensional convolution layers with a series of dimension-reducing layers that output directly into the fully connected layers.

9. The system of claim 6, wherein the system further comprises a training engine executable on the processor according to software instructions stored in the memory device, wherein the training engine is configured to:
  generate a plurality of embeddings of suboptimal candidate variation information, wherein the information comprises a plurality of sequence reads, and an embedding of a model reference sequence;
  process the embeddings with a deep learning model that detects the suboptimal candidate variation; and
  minimize error in the detection of the suboptimal candidate variation relative to a ground truth candidate variation of the model reference sequence by adjusting parameters of the deep learning model.

10. The system of claim 9, wherein the deep learning model is configured to:
  transform the embeddings of suboptimal candidate variation information with a series of 1-dimensional convolution layers;
  max and mean pool the output of the series of 1-dimensional convolution layers; and
  transform the output of max and mean pooling with a series of fully connected layers that output detection of the suboptimal candidate variation.

11. A non-transitory computer-readable medium comprising instructions for detecting candidate variations in a biopolymer sequence relative to a reference sequence that, when executed by a processor, cause the processor to perform one or more steps comprising:
  generating embeddings of at least one million sequence reads obtained by sequencing a sample of the biopolymer at less than 10× coverage, each read corresponding to a region of at least 200 bp of the biopolymer sequence, wherein each embedding of a sequence read is concatenated with an embedding of a corresponding reference sequence; and
  detecting one or more candidate variations in the biopolymer sequence based at least in part on the embeddings of the at least one million sequence reads, wherein detecting comprises processing the embeddings with a deep learning model comprising a series of 1-dimensional convolution layers, wherein a mean pooling of one or more outputs from at least one of the 1-dimensional convolution layers is added back to the one or more outputs from the same at least one 1-dimensional layers before it is input into the subsequent 1-dimensional convolution layer, and max and mean pooling the output of the series of 1-dimensional convolution layers.

12. The non-transitory computer-readable medium of claim 11, wherein the embeddings further comprise sequence quality information, sequence positional information, and/or variation hypothesis information.

13. The non-transitory computer-readable medium of claim 11, wherein processing the embeddings with a deep learning model further comprises:
  transforming the one or more outputs from at least one of the series of 1-dimensional convolution layers with a series of dimension-reducing layers that output directly into the fully connected layers.

14. The non-transitory computer-readable medium of claim 11, wherein the medium comprises instructions for training the deep learning model, wherein training comprises:
  generating a plurality of embeddings of suboptimal candidate variation information, wherein the information comprises a plurality of sequence reads, and an embedding of a model reference sequence;
  processing the embeddings of suboptimal candidate variation information with a deep learning model that detects the suboptimal candidate variation; and
  minimizing error in the detection of the suboptimal candidate variation relative to a ground truth candidate variation of the model reference sequence by adjusting parameters of the deep learning model.

* * * * *